US00PP17656P2

(12) United States Plant Patent
van Noort

(10) Patent No.: US PP17,656 P2
(45) Date of Patent: Apr. 24, 2007

(54) ***GERANIUM* PLANT NAMED 'PINK PENNY'**

(50) Latin Name: *Geranium wallichianum*
Varietal Denomination: Pink Penny

(76) Inventor: Marco van Noort, Wasbeeklaan 13, Warmond (NL), 2361 HG ( * ) Notice: Subject to any disclaimer, the term of this patent is extended or adjusted under 35 U.S.C. 154(b) by 0 days.

(21) Appl. No.: 11/291,372

(22) Filed: Dec. 1, 2005

(51) Int. Cl.
*A01H 5/00* (2006.01)

(52) U.S. Cl. ..... Plt./328

(58) Field of Classification Search ..... Plt./328
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Geranium wallichianum,* 'Pink Penny', characterized by its abundant, large pink flowers, its long blooming season, its marbled green foliage, and its spreading growth habit with good performance as a groundcover.

2 Drawing Sheets

Botanical classification: *Geranium wallichianum.*
Cultivar designation: 'Pink Penny'.

BACKGROUND OF THE INVENTION

The present invention relates to a new and distinct cultivar of *Geranium* plant, botanically known as *Geranium wallichianum* 'Pink Penny' and will be referred to hereafter by its cultivar name, 'Pink Penny'.

The inventor discovered the new cultivar, 'Pink Penny', in a cultivated growing area at his nursery in Warmond, The Netherlands in July of 2002. 'Pink Penny' was discovered as a whole plant mutation from repeated selections of seedlings that originated from seeds of unnamed pink flowering plants of *Geranium wallichianum.*

The new cultivar, 'Pink Penny', was selected as unique for its abundant large pink flowers and its long blooming habit. 'Pink Penny' can be most closely compared to *Geranium wallichianum* 'Buxton's Variety' (not patented) for its long blooming habit. 'Buxton's Variety' differs in particular in having blue flowers, whereas 'Pink Penny' blooms with pink flowers.

Asexual reproduction of the new cultivar was first accomplished by division in Warmond, The Netherlands in 2003 by the inventor. Propagation by division and subsequently by tissue culture has determined that the characteristics of this cultivar are stable and are reproduced true to type in successive generations.

SUMMARY OF THE INVENTION

The following traits have been repeatedly observed and represent the characteristics of 'Pink Penny'. These attributes in combination distinguish 'Pink Penny' as a new and distinct cultivar of *Geranium.*

1. 'Pink Penny' has large flowers with an average diameter of 3.5 cm.
2. The flower color of 'Pink Penny' is pink with dark purple veining.
3. 'Pink Penny' blooms abundantly with a long blooming season; blooming from mid May to late September in The Netherlands.

4. The foliage of 'Pink Penny' is medium green in color with lighter green marbling.
5. The plant habit of 'Pink Penny' is prostrate with suitable use as a groundcover.
6. 'Pink Penny' propagated with easy by division or tissue culture.
7. Cold hardy to at least USDA Zone 5.

BRIEF DESCRIPTION OF THE DRAWING

The accompanying colored photographs illustrate the overall appearance and distinct characteristics of the new *Geranium.* The photographs were taken of two year-old plants of 'Pink Penny' as grown outdoors in a field plot in The Netherlands.

The photograph in FIG. 1 is a view of a plant of 'Pink Penny' in bloom.

Figure 1:
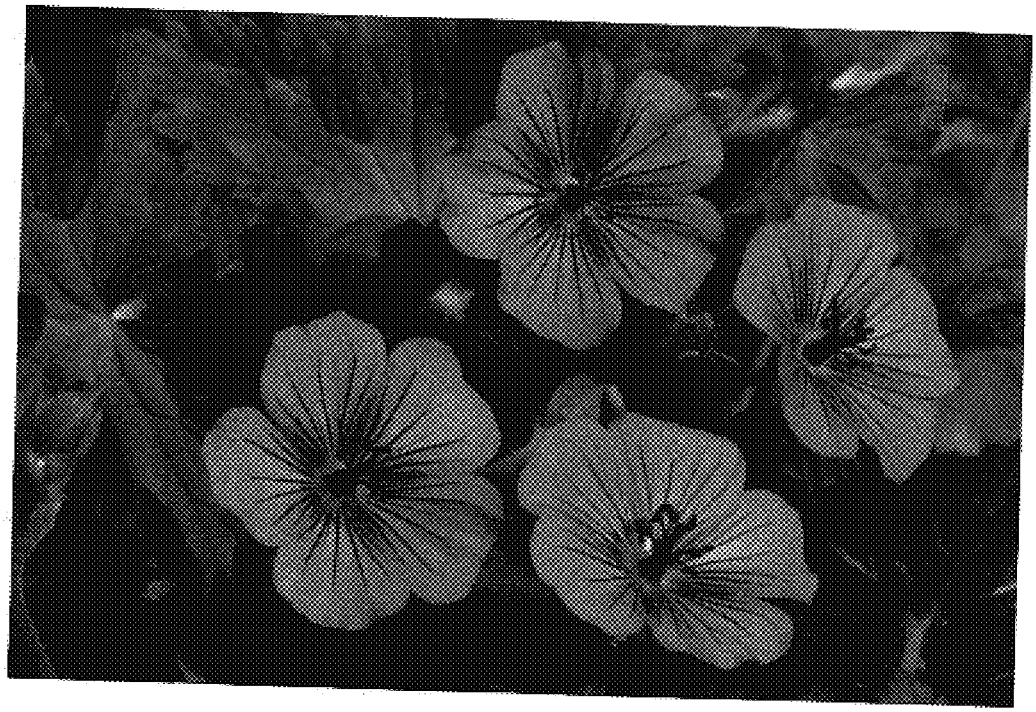
Figure 2:
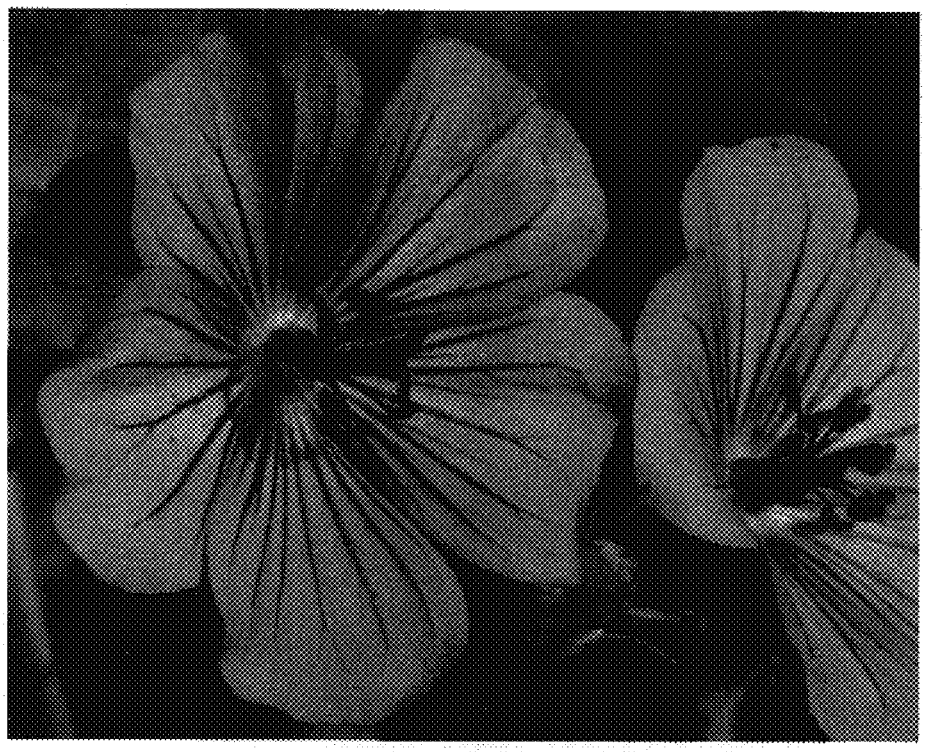
Figure 3:
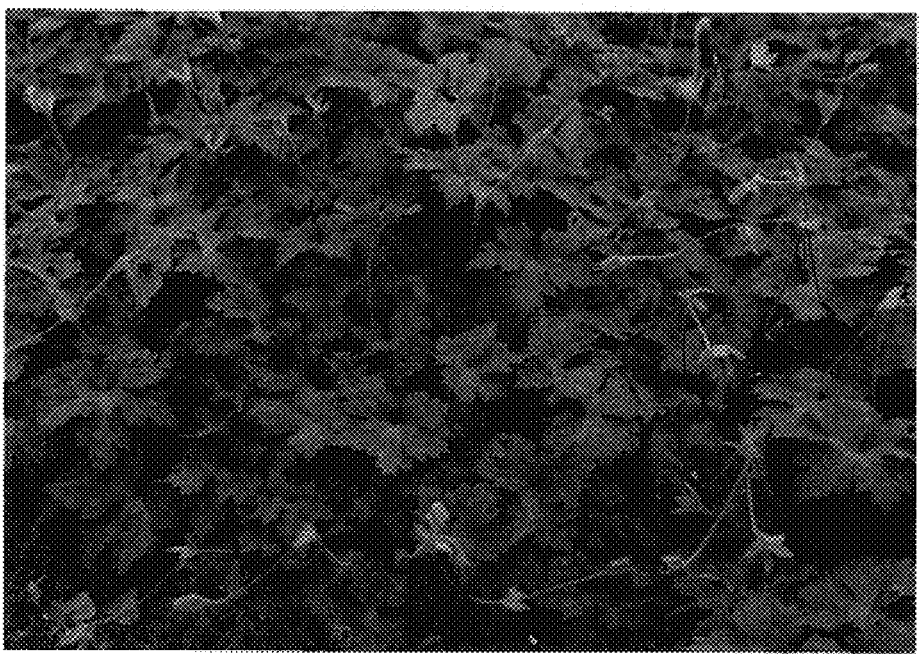

The photograph in FIG. 2 is of a close-up view of the flowers of 'Pink Penny' while the photograph in FIG. 3 provides a view of the growth habit of 'Pink Penny'.

The colors in the photographs are as close as possible with the photographic and printing technology utilized. The color values cited in the detailed botanical description accurately describe the colors of the new *Geranium.*

DETAILED BOTANICAL DESCRIPTION OF THE PLANT

The following is a detailed description of 2 year-old, field grown plants of the new cultivar as grown outdoors in Warmond, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Pink Penny' is a cultivar of *Geranium wallichianum.*

Parentage: Naturally whole plant mutation from seeds derived from unnamed selections of *Geranium wallichianum.*

General characteristics:

*Blooming period.*—Mid May to late September in The Netherlands.

*Plant habit.*—Herbaceous perennial with broadly spreading growth habit.

*Height and spread.*—Reaches about 17 cm in height and about 1 m in spread.

*Cold hardiness.*—At least to U.S.D.A. Zone 5.

*Heat tolerance.*—At least tolerant to temperature up to 35° C.

*Diseases and pests.*—No susceptibility or resistance to diseases or pests has been observed for 'Pink Penny'.

*Root description.*—Fibrous roots extending from stout rootstock.

*Branching habit.*—Freely branched, about 28 lateral branches on a 2 year-old plant.

Growth and propagation:

*Growth rate.*—Moderate to vigorous, growth rate is stems is about 15 cm per month in spring.

*Propagation.*—Division and *In vitro* propagation.

*Time required for root initiation.*—4 weeks from tissue culture popagule.

*Time required for root description.*—A rooted tissue culture plug requires about 6 weeks under mist in the greenhouse to harden off and another 8 to 10 weeks of outdoor production until flowering.

Stem description:

*Stem size.*—Average of 37 cm in length and 3 mm in width, stems are thickened at nodes at a average of 4.5 mm.

*Stem shape.*—Round.

*Stem color.*—Young stems and under sides of mature stems 144B, upper surface of mature stems and old stems 183B.

*Stem surface.*—Slightly glossy.

*Internode length.*—Average of 9 cm.

Foliage description:

*Leaf shape.*—Orbicular to reniform.

*Leaf division.*—Simple.

*Leaf base.*—Hastate.

*Leaf apex.*—Acute.

*Leaf venation.*—Palmate, 143A in color on upper surface and 144A on lower surface.

*Leaf margins.*—Palmately parted, lobes biserrate.

*Leaf attachment.*—Petiolate.

*Leaf arrangement.*—Alternate.

*Leaf surface.*—Upper surface is dull and very sparsely densely covered with short hairs about 0.75 mm in length and 155D in color, lower surface is pubescent only on veins that are densely covered with short bristly hairs about 0.75 mm in length and 155D in color.

*Leaf color.*—Young upper surface, color between 137B and 141A with lighter marbling of 145A, young lower surface; color between 141A and 146B, mature upper surface; 143A with marbling of 145A, mature lower surface; a color between 144A and 146C.

*Leaf size.*—Average of 4.4 cm in length and 4.6 cm in width.

*Leaf quantity.*—Average of 9 per lateral branch.

*Petiole size.*—Average of 3.8 cm in length and 1.2 mm in width.

*Petiole color.*—175Ato 175B on upper surface, 144A on lower surface.

*Stipules.*—Two at each node, ovate in shape, rounded apex, broadly cuneate base, average of 1.3 cm in length and 9 mm in width, 145A in color with tips of 47A to 47B.

Flower description:

*Inflorescence type.*—Single, rotate, pink flowers with purple veins, arranged in pairs.

*Lastingness of flowers.*—About 7 days, self cleaning.

*Flower size.*—Average of 1.2 cm in height and 3.5 cm in diameter.

*Flower fragrance.*—None.

*Flower number.*—Average of 20 per inflorescence (10 pairs), about 560 per plant.

*Flower aspect.*—Upright to outward.

*Flower bud size.*—Average of 9.5 mm in length, up to 4.5 mm in width.

*Flower bud color.*—138B.

*Flower bud shape.*—Elliptic.

*Corolla features.*—Petals are unfused and arranged in a rotate form.

*Petal number.*—5.

*Petal shape.*—Obcordate.

*Petal color.*—Opening, upper surface; N78B with veins N79B, opening, lower surface; N78B with veins N79C, fully open, upper surface; N78B with veins N79B, fully open, lower surface; N78B (slightly more reddish) with veins N79C, fading, upper and lower surface; N78B to N78C with veins N79C.

*Petal surface.*—Glabrous.

*Petal margins.*—Entire.

*Petal apex.*—Obtuse.

*Petal size.*—Average of 1.7 cm in length and 1.5 cm in width.

*Calyx form.*—Rotate, slightly cupped.

*Calyx size.*—Average of 5 mm in length and 1.7 cm in width.

*Sepal number.*—Average of 5.

*Sepal shape.*—Elliptic.

*Sepal margin.*—Entire.

*Sepal size.*—Average of 1 cm length, 3 mm in width.

*Sepal surface.*—Glabrous, under side covered with short hairs (hairs have an average length of 0.75 mm and are N155A in color).

*Sepal apex.*—Aristate.

*Sepal base.*—Cuneate.

*Sepal color.*—Opening: 143B on upper surface and 138B to 143B on lower surface; Fully open: 143B on upper surface and lower surface.

*Peduncle size.*—Average of 5 cm in length and 1.5 mm in diameter.

*Peduncle strength/aspect.*—Strong, held at about a 40° angle relative to lateral branch.

*Peduncle size.*—Round.

*Peduncle color.*—175A to 175B on upper side, 144B on lower side.

*Pedicel size.*—Average of 3.9 cm in length and1 mm in width.

*Pedicel shape.*—Round.

*Pedicel strength/aspect.*—Moderately strong, lateral flowers are held at about 20° relative to peduncle.

*Pedicel color.*—175A to 175B on upper side, 144B on lower side.

Reproductive organs:

*Gynoecium.*—1 pistil, about 8 mm in length, 5 stigmas are decurrent and N79B to N79C in color, style is about 3 mm in length and 144C in color, ovary is 144C to 144D in color and densely covered with very short (about 0.3 mm) hairs N155A in color.

*Androcoecium.*—10 strands, anthers are dorsifixed, oblong in shape, curled, 2 mm in length, 0.75 mm in width, and 186A to 202A in color, filament is 7 mm in length and 61A in color, pollen is low in abundant and 196D in color.

*Fruit/seeds.*—Fruit comprised of rostrum and 5 mericarps (typical cranesbill form), 3.4 cm in length, 5 mm in width with a base N170B in color and beaks N199A to N199B in color. Seeds, 5 per fruit, 3 mm in length, 1.75 mm in width and 200A in color.

I claim:

1. A new and distinct cultivar of *Geranium* plant named 'Pink Penny' as herein illustrated and described.

* * * * *